United States Patent [19]
Dydyk et al.

[11] Patent Number: 5,658,810
[45] Date of Patent: Aug. 19, 1997

[54] METHOD OF MAKING A SENSOR FOR DETERMINING A RATIO OF MATERIALS IN A MIXTURE

[75] Inventors: Michael Dydyk, Scottsdale; John S. Escher, Paradise Valley, both of Ariz.

[73] Assignee: Motorola, Schaumburg, Ill.

[21] Appl. No.: 563,432

[22] Filed: Nov. 24, 1995

Related U.S. Application Data

[62] Division of Ser. No. 223,068, Apr. 4, 1994, Pat. No. 5,500,543.

[51] Int. Cl.$^6$ .................................................. H01L 21/82
[52] U.S. Cl. .................................................. 438/49
[58] Field of Search ............................ 437/40 R, 40 GS, 437/41 R, 41 GS, 51, 54, 59; 257/253, 414

[56] References Cited

U.S. PATENT DOCUMENTS

| | | | |
|---|---|---|---|
| 4,437,969 | 3/1984 | Covington et al. | 257/253 |
| 4,453,125 | 6/1984 | Kimura et al. | 324/637 |

FOREIGN PATENT DOCUMENTS

| | | | |
|---|---|---|---|
| 55-151372 | 11/1980 | Japan | 257/277 |
| 56-6467 | 1/1981 | Japan | 257/277 |
| 62-224948 | 10/1987 | Japan . | |
| 63-78070 | 4/1988 | Japan . | |
| 1-124757 | 5/1989 | Japan | 257/253 |

OTHER PUBLICATIONS

P. Enoksson et al., J. Microelectromech. Syst. 5(1)(1996)39 "Vibrating Modes of a Resonant Silicon Tube Density Sensor" Mar. 1996.

*Primary Examiner*—Charles C. Bowers, Jr.
*Assistant Examiner*—Leon Radomsky
*Attorney, Agent, or Firm*—Eugene A. Parsons

[57] ABSTRACT

A sensor (10, 40) for measuring the ratio of fluids or other materials in mixture (12) utilizes a coplanar resonator. The resonator has an outer conductor or conductor plane (17, 41) that is on a semiconductor substrate (11). The conductor plane (17, 41) has an opening (18, 48) that exposes a portion of the surface of the substrate. An inner conductor or sensing element (19, 42) is formed on the exposed surface within the opening (18, 48) so that the conductor plane (17, 41) and the sensing element (19, 42) are coplanar. The sensing element (19, 42) is coupled to an input (22) of a transistor (21) to form an oscillator. The oscillator frequency varies as the ratio of materials in the mixture (12) varies.

6 Claims, 4 Drawing Sheets

METHOD OF MAKING A SENSOR FOR DETERMINING A RATIO OF MATERIALS IN A MIXTURE

This is a division of application Ser. No. 08/223,068, filed Apr. 4, 1994, U.S. Pat. No. 5,500,543.

BACKGROUND OF THE INVENTION

The present invention relates, in general, to sensors, and more particularly, to a novel coplanar resonator sensor.

Previously, microwave resonators have been used for a variety of sensor applications including sensors for measuring the thickness of materials. These prior sensors typically utilize two parallel conductors wherein the material to be measured is inserted between the two conductors. The conductors and the material to be measured form a capacitor that controls the frequency of an R.F. oscillator. Because the material to be measured is positioned between the parallel conductors, the type of material effects the amplitude of the output signal from the oscillator. Often, the material to be measured is a mixture of two components. As the ratio of the two components varies, the amplitude of the output signal from the oscillator also varies. The oscillator output signal amplitude can vary by up to 40 to 45 db for some material variations. In order to reduce the amplitude variations, the output signal of the oscillator is applied to a power limiter circuit prior to applying the signal to other circuits. The power limiter circuit increases the cost and the complexity of a system utilizing the sensor.

Accordingly, it is desirable to have a sensor that does not require positioning the material to be measured between the conductors of the sensor, and that has an output signal variation of less than 40 db as the components of the material to be measured varies.

DETAILED DESCRIPTION OF THE DRAWINGS

Figure 1:
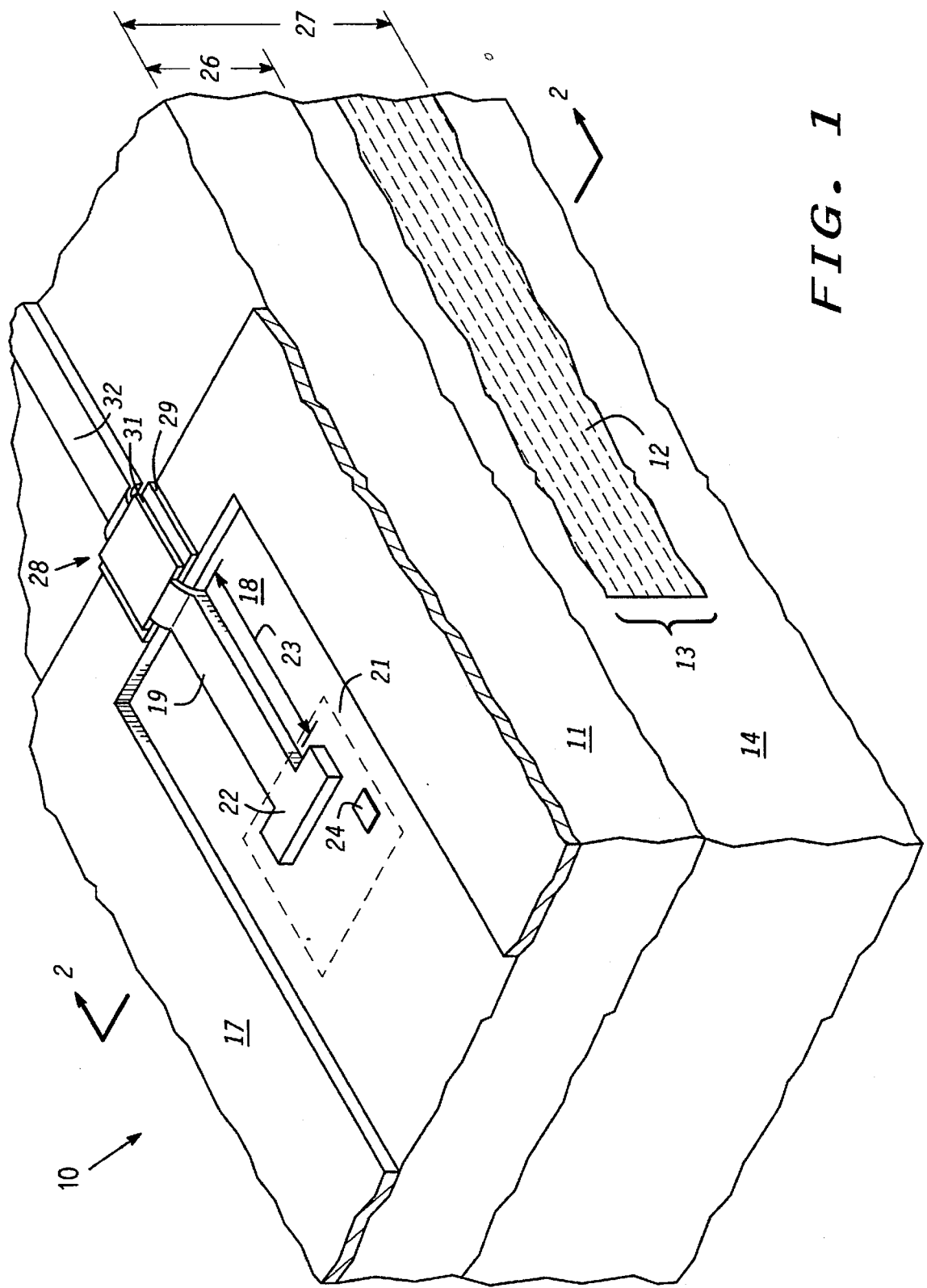
FIG. 1 illustrates an enlarged perspective cutaway view of a sensor in accordance with the present invention.

FIG. 1 is an enlarged perspective view of a sensor 10 that is suitable for measuring the ratio of fluids or other materials that are combined in a mixture 12. For example, sensor 10 may be utilized to measure the ratio of gasoline and alcohol in a gasoline-alcohol mixture such as may be utilized as a fuel in an internal combustion engine. Sensor 10 includes a non-conducting substrate 11 having a thickness 26. Substrate 11 can be a variety of non-conducting materials including semiconductor materials such as silicon and gallium arsenide, alumna, and silicon nitride. Sensor 10 utilizes a coplanar resonator that is coupled to an active semiconductor device in order to form an oscillator. The coplanar resonator includes a conductor plane or outer conductor 17 and an inner conductor strip or sensing element 19. Conductor 17 is formed on a first or top surface of substrate 11 and has a cavity or opening 18 that exposes a portion of the surface of substrate 11. Element 19 is formed on the top surface of substrate 11 within opening 18. An active semiconductor device 21, illustrated within by a dashed box, is formed on the surface of substrate 11 so that device 21 is within opening 18. Device 21 has a first conducting electrode or output 24 connected (not shown) to other electronic components (not shown) as will be seen hereinafter. A second conducting electrode (not shown) is connected to conductor 17. Typically, conductor 17 is a D.C. return or ground potential. An input 22 of device 21 is connected to a first end of element 19 thereby electrically coupling element 19 to input 22.

An R.F. capacitor 28 is utilized to provide a short circuit between element 19 and conductor 17 at R.F. frequencies, for example above one hundred megahertz (MHz), while electrically isolating element 19 from conductor 17 at low frequencies, for example below one hundred kilohertz (KHz). Thus, capacitor 28 allows an external conductor 32 to supply a D.C. voltage through element 19 to input 21, while isolating the D.C. voltage from conductor 17. Capacitor 28 includes a dielectric layer 29 that is on the surface of conductor 17 and a top conductor or top plate 31 that is on dielectric layer 29. Conductor 17 functions as the bottom conductor or plate of capacitor 28. Element 19 is connected to conductor 32 by plate 31. A second end of element 19 is connected to plate 31 by an air bridge, or other similar means, so that element 19 does not touch physically conductor 17. Similarly, conductor 32 is also connected to plate 31. Techniques for forming air bridges are well known to those skilled in the semiconductor art.

In the preferred embodiment, device 21 is an R.F. MESFET (metal-semiconductor field effect transistor) having a cut off frequency in excess of ten gigahertz (GHz). Consequently, conductor 17 is connected to a source of device 21, and output 24 is a drain of device 21. Also, substrate 11 is gallium arsenide (GaAs), and gold is used for conductor 17, element 19, and plate 31.

Typically, sensor 10 is placed on a pipe or conduit 14 that has an opening 13 for containing mixture 12. A height 27 represents the thickness of substrate 11 and the height of mixture 12. As the ratio of materials in the mixture vary, the dielectric constant of the mixture also varies causing the oscillator frequency to change. Because to the coplanar configuration, neither element 19 non conductor 17 directly contact mixture 12. Therefore, changes in the ratio of materials in mixture 12 are decoupled from sensor 10 so that amplitude variations in the output of device 21 resulting from the ratio changes are much lower than those of prior sensors. In order to allow element 19 to sense mixture 12, it is important that the material underlying element 19, e.g. between element 19 and mixture 12, is not a conductor. Thus, the portion of conduit 14 underlying element 19 must be non-conducting, and the surface of substrate 11 that underlies element 19 must not be covered by a conductor. Conduit 14 could be a metal conduit having a non-conducting window underlying element 19. For example, conduit 14 could be copper with a quartz window or insert underlying element 19. In the preferred embodiment, conduit 14 is plastic.

The reactance looking into sensor 10 is selected to resonate the input reactance of device 21 at the frequency of operation. The reactance looking into resonator 10 is given by:

$$X = \frac{Z_{air}}{\sqrt{\epsilon_{r1}\dfrac{1}{1+\dfrac{t}{h}\left(\dfrac{\epsilon_{r1}}{\epsilon_{r2}}-1\right)}}} \tan\frac{2\Pi L\sqrt{\epsilon_{r1}\dfrac{1}{1+\dfrac{t}{h}\left(\dfrac{\epsilon_{r1}}{\epsilon_{r2}}-1\right)}}}{\lambda_g}$$

where;

$\epsilon_{r1}$=relative dielectric constant of the material used for substrate 11

$\epsilon_{r2}$=relative dielectric constant of mixture 12

$\lambda_g$=the operating frequency wavelength

X=the reactance looking into sensor 10

$Z_{air}$=the impedance of a coplanar waveguide with an air dielectric t=thickness 26 h=height 27 and

L=length 23.

For example, for a resonator formed on a GaAs substrate and having an oscillator frequency of approximately two GHz, L is approximately 14,580 microns, t is approximately 100–400 microns, and h is approximately 400–6000 microns. For such a resonator, element 19 is approximately seventy-five microns wide and each long side of element 19 is approximately fifty-five microns from the side of opening 18.

Figure 2:
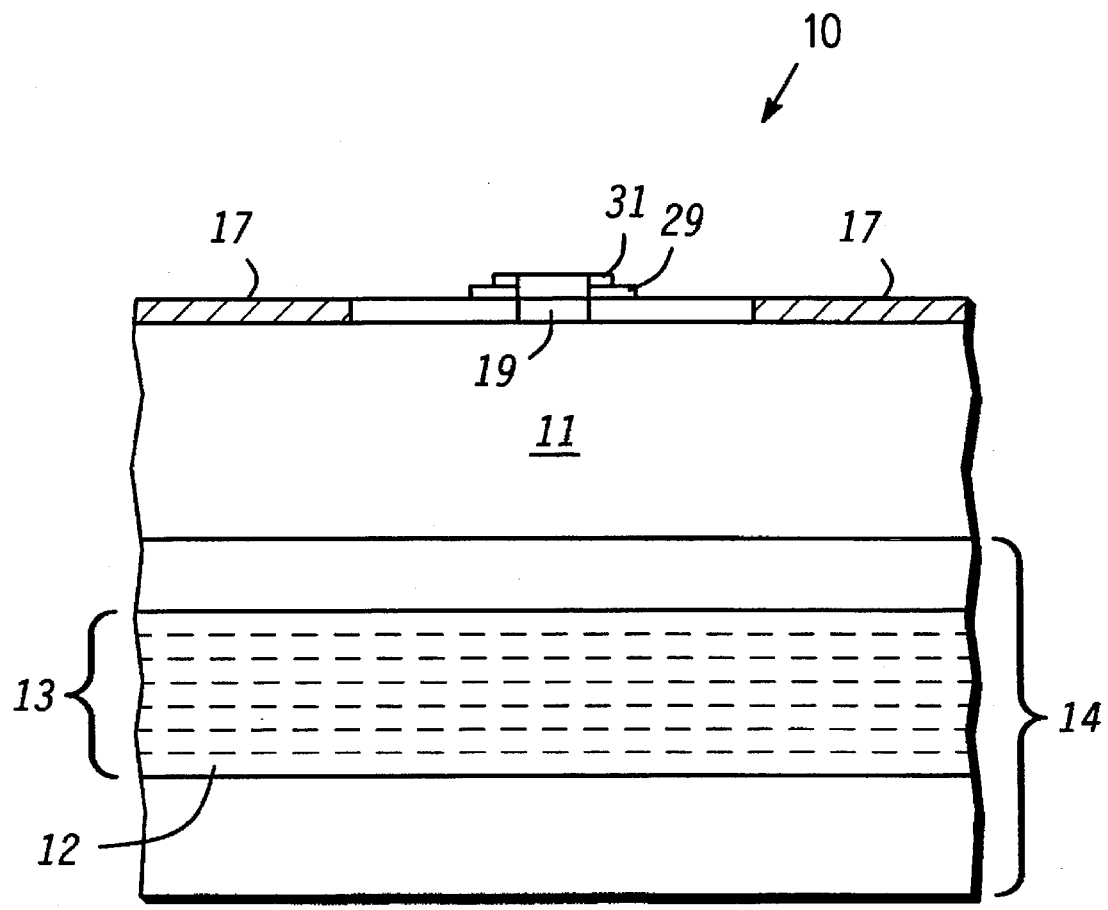
FIG. 2 is a cross-sectional view of the sensor of FIG. 1 in accordance with the present invention.

FIG. 2 illustrates a cross-sectional view of sensor 10 along cross-sectional line 2—2 shown in FIG. 1. Elements of FIG. 2 that are the same as FIG. 1 have the same reference numerals. FIG. 2 illustrates that the material underlying element 19 is devoid of a conductor.

Figure 3:
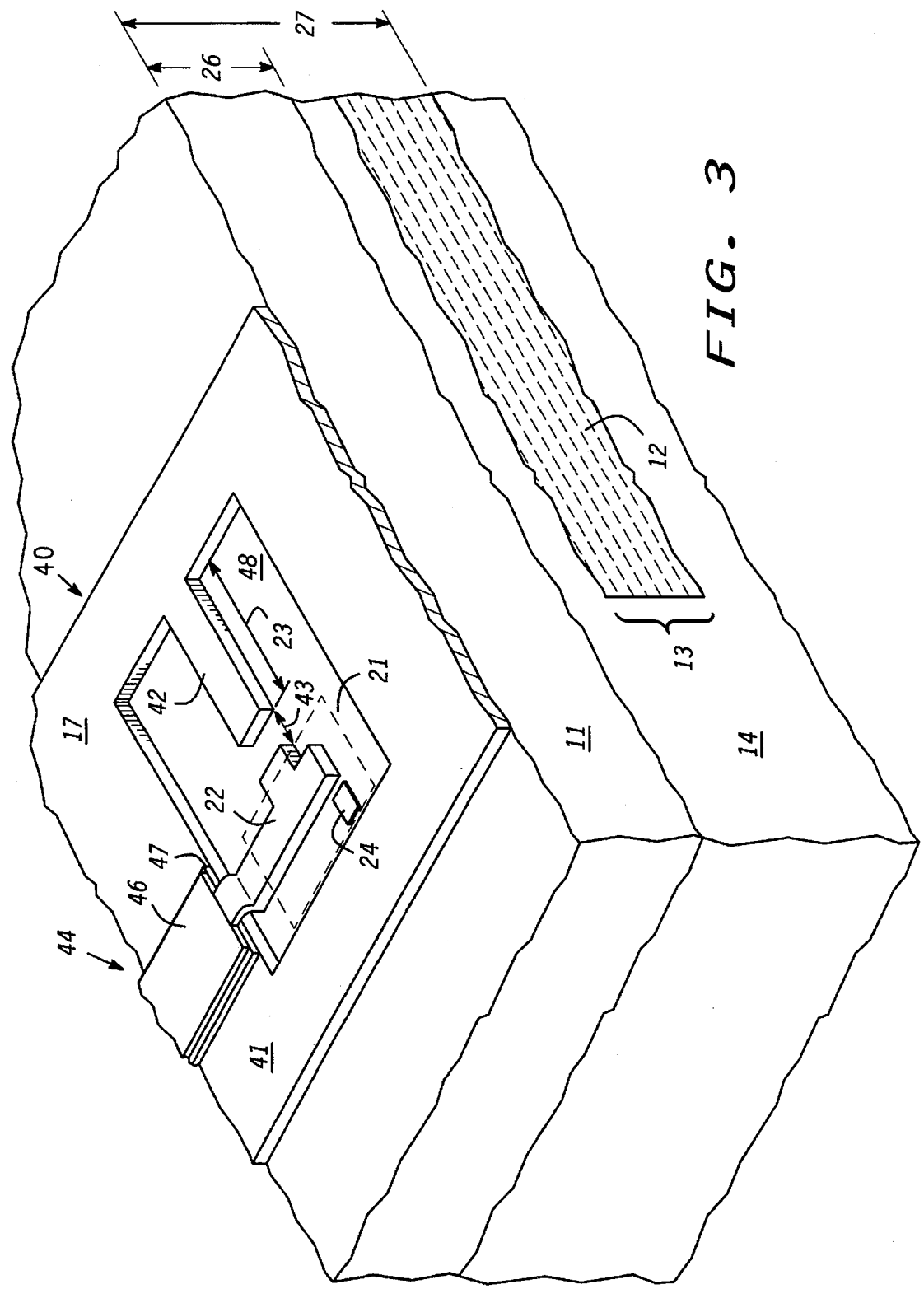
FIG. 3 is an enlarged cutaway perspective view of an alternate embodiment of a sensor in accordance with the present invention.

FIG. 3 illustrates a sensor 40 that is an alternate embodiment of sensor 10 shown in FIG. 1. Elements of FIG. 3 that are the same as FIG. 1 have the same reference numerals. Sensor 40 has a conductor plane or outer conductor 41 having an opening or cavity 48 that exposes a portion of the surface of substrate 11. An inner conductor or sensing element 42 projects from a side of conductor 41 into cavity 48. Element 42 is separated from input 22 of device 21 by a gap 43. Gap 43 could also be an R.F. capacitor having one plate connected to the end of element 42 and a second plated connected to input 22. An R.F. capacitor 44, similar to capacitor 28 of FIG. 1, is used to couple a D.C. voltage to input 22. Capacitor 44 has a top plate 46 and a dielectric layer 47 while conductor 41 forms a bottom plate of capacitor 44. Sensor 40 functions similarly to sensor 10 of FIG. 1.

Figure 4:
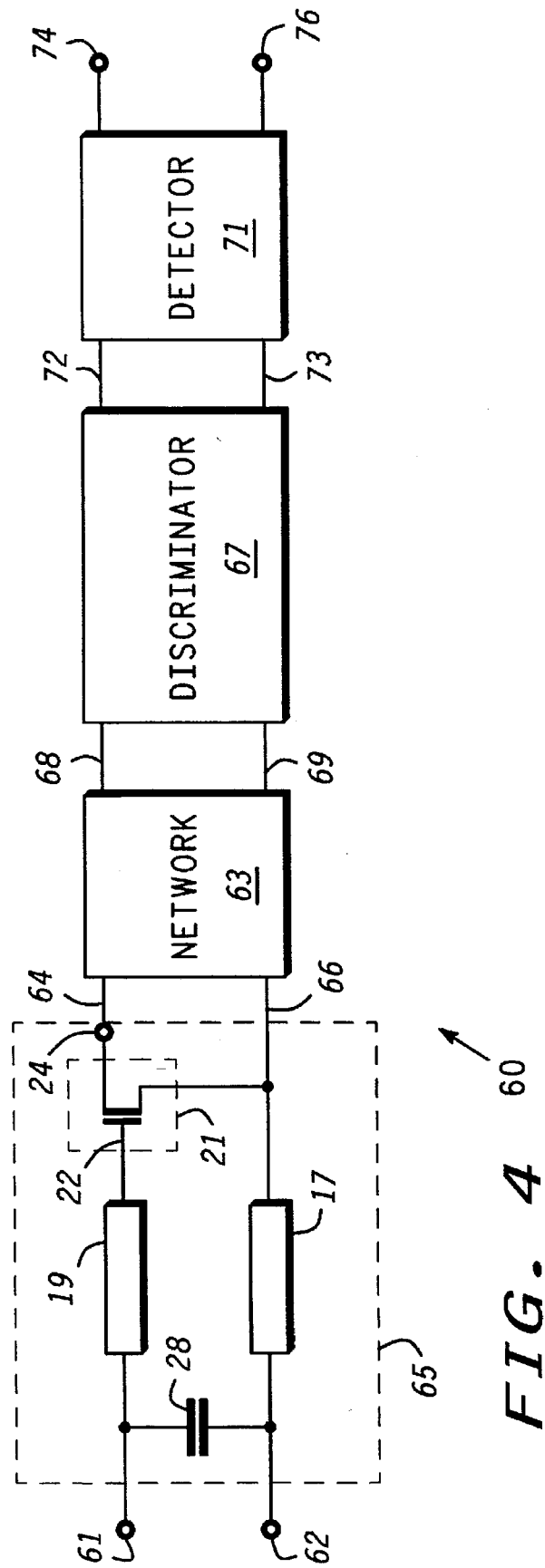
FIG. 4 schematically illustrates a circuit utilizing the sensors of FIG. 1 and FIG. 3 in accordance with the present invention.

FIG. 4. schematically illustrates a circuit 60 that includes an equivalent circuit 65, shown in a dashed box, of sensor 10 (FIG. 1), and other circuitry that may be connected to sensor 10. Elements of FIG. 4 that are the same as FIG. 1 have the same reference numerals. Circuit 65 includes R.F. capacitor 28, element 19, conductor plane 17, and active device 21, shown within a dashed box. An input 61 to circuit 60 represents external conductor 32 and is utilized to apply the D.C. voltage to circuit 65. An input 62 represents a connection between conductor 17 and ground. Capacitor 28 forms an R.F. short between element 19 and conductor 17 while isolating conductor 17 from the D.C. voltage applied to input 61. Conductor 17 is coupled to a source of device 21. Consequently, the source of device 21 and input 22 are electrically loaded with conductor 17 and element 19 of the resonator.

Output 24 of device 21 is connected to an input 64 of an impedance matching network 63 while an input 66 of network 63 is connected to the source of device 21. The outputs of network 63 are connected to inputs 68 and 69 of a discriminator 67 which is tuned to the oscillation frequency of device 21. The outputs of discriminator 67 are connected to inputs 72 and 73 of a detector 71 that provides a rectified waveform on outputs 74 and 76.

Because of the coplanar configuration of sensor 10 (FIG. 1) the amplitude of the signal on inputs 64 and 66 have an amplitude variation of less than approximately twenty db which is much less than the typical forty to forty-five db amplitude variations of prior circuits. Because of this small amplitude variation, the output signal of sensor 10 does not have to be applied to a power limiting circuit. Thus, circuit 60 is simpler and less expensive than circuits required for prior sensors.

By now it should be appreciated that a novel sensor has been provided. By forming the sensing elements in the same plane, the sensor is decoupled from variations in the materials of the mixture to be measured thereby minimizing amplitude variations in the sensor output signal. Consequently, power limiting circuits are not required thereby resulting in a low cost, easy to manufacture circuit for processing the sensor output signal. The sensor can be utilized for sensing a variety of materials including, but not limited to, sensing the ratio of gasoline and alcohol in a gasoline-alcohol mixture such as may be utilized as a fuel in an internal combustion engine.

We claim:

1. A method of forming a coplanar resonator sensor comprising:

providing a mixture to be sensed;

forming a sensing element of the sensor coplanar to a conductor plane of the sensor and overlying the mixture; and coupling an input of a semiconductor device to the sensing element.

2. The method of claim 1 further including using the sensing element for applying a D.C. voltage to the input.

3. The method of claim 1 further including forming the sensing element, the conductor plane, and the semiconductor device on a semiconductor substrate.

4. The method of claim 1 wherein forming the sensing element of the sensor coplanar to the conductor plane includes forming the conductor plane to have an opening with the sensing element projecting into the opening from a side of the opening.

5. The method of claim 1 wherein forming the sensing element of the sensor coplanar to the conductor plane includes forming the conductor plane to have an opening with the sensing element within the opening.

6. The method of claim 1 further including forming the sensing element and the conductor plane on a substrate that is one of alumina, silicon nitride, or a semiconductor material.

* * * * *